US012082554B2

(12) United States Patent
Rooda et al.

(10) Patent No.: US 12,082,554 B2
(45) Date of Patent: Sep. 10, 2024

(54) WEARABLE DEVICE FOR MONITORING THE HEALTH OF AN ANIMAL

(71) Applicant: SwineTech, Inc., Cedar Rapids, IA (US)

(72) Inventors: Matthew Rooda, New Sharon, IA (US); John Rourke, Cedar Rapids, IA (US); Abraham Espinoza, North Liberty, IA (US)

(73) Assignee: SwineTech, Inc., Solon, IA (US)

( * ) Notice: Subject to any disclaimer, the term of this patent is extended or adjusted under 35 U.S.C. 154(b) by 693 days.

(21) Appl. No.: 16/585,724

(22) Filed: Sep. 27, 2019

(65) Prior Publication Data

US 2020/0100463 A1 Apr. 2, 2020

Related U.S. Application Data

(60) Provisional application No. 62/737,978, filed on Sep. 28, 2018.

(51) Int. Cl.
| *A01K 11/00* | (2006.01) |
| *A01K 1/02* | (2006.01) |
| *A61B 5/00* | (2006.01) |
| *A61D 9/00* | (2006.01) |

(52) U.S. Cl.
CPC .......... *A01K 11/006* (2013.01); *A01K 1/0218* (2013.01); *A61B 5/746* (2013.01); *A61B 5/6802* (2013.01); *A61B 5/6833* (2013.01); *A61D 9/00* (2013.01)

(58) Field of Classification Search
CPC .. A01K 11/006; A01K 11/0218; A61B 5/746; A61B 5/6802; A61B 5/6833; A61D 9/00
See application file for complete search history.

(56) References Cited

U.S. PATENT DOCUMENTS

| 6,550,652 B2 * | 4/2003 | Whitaker | A01K 11/00 224/191 |
| 8,714,113 B2 * | 5/2014 | Lee, IV | A01K 15/022 119/718 |
| 9,017,256 B2 * | 4/2015 | Gottesman | A61B 5/02028 600/300 |
| 9,486,167 B2 * | 11/2016 | Martinez | A61B 5/0002 |
| 10,772,522 B2 * | 9/2020 | Zadig | A61B 5/332 |
| 11,259,501 B2 * | 3/2022 | Espinoza | A01K 29/005 |
| 11,666,229 B2 * | 6/2023 | Murali | A61B 5/7257 600/301 |
| 2020/0329663 A1 * | 10/2020 | Espinoza | A01K 29/005 |

FOREIGN PATENT DOCUMENTS

| WO | 0060979 A1 | 10/2000 |
| WO | WO-2016205098 A1 * | 12/2016 |

\* cited by examiner

*Primary Examiner* — Franklin D Balseca
(74) *Attorney, Agent, or Firm* — SHUTTLEWORTH & INGERSOLL, PLC; Jason R. Sytsma

(57) ABSTRACT

A housing structure with an opening and an adhesive is combined to the bottom of the housing structure for adhering the housing structure to the skin of an animal. A pocket accessible through the opening in the housing structure for inserting and holding a warning device in direct contact with the skin of the animal through the opening. The housing structure of the adhesive patch can comprise a base layer comprising a bottom side on which the adhesive layer is attached.

10 Claims, 5 Drawing Sheets

WEARABLE DEVICE FOR MONITORING THE HEALTH OF AN ANIMAL

CROSS-REFERENCE TO RELATED APPLICATIONS

The present application claims the benefit of provisional application Ser. No. 62/737,978 filed on Sep. 28, 2018, which is incorporated by reference herein.

TECHNICAL FIELD

This disclosure relates generally to a warning system for monitoring the health of an animal, and more particularly to a disposable housing structure in the form of an adhesive patch for supporting a removable device that interacts with the warning system.

BACKGROUND INFORMATION

In animal farrowing, there is always the problem of the mother crushing the newly born feeder when the mother lies down or when, while lying down, she changes from one position to another; for example, pre-weaned piglet mortality, as a result of being crushed by the sow in a farrowing enclosure, accounts for a 7% to 10% loss of all piglets that are farrowed. This loss translates into reduced potential profits for the pork producer.

Attempts have been made to solve this problem with electrical or electronic sensing and devices that detect noise from the squealing feeder followed by an electrical impulse to the mother to cause her to switch positions, hopefully off of the endangered feeder. Such devices have previously relied on a stored acoustical signal of a squealing feeder to compare with the sound from the endangered, squealing feeder. Feeders, however, rarely make the same sound, especially as they age (even from day to day after birth) or across breeds. A piglet, for example, that is one day old sounds very different than a piglet two, three, or four days old. Piglets of different breeds sound different too. Furthermore, when such devices are put into practice where there are dozens of sows and hundreds of piglets in an enclosed confinement building comprising a myriad of structures, concrete floor, and aluminum and steel siding and frame, the acoustics of the confinement building present a non-trivial problem to overcome.

The danger period for the piglet is the first two days after birth. This means that for warning systems attached to the mother, they need only be attached for those first few days. Therefore, what is needed is an affordable structure for attaching a warning system to the mother in a safe and reliable way that can be easily or quickly inserted and removed from the adhesive-backed for cost-effective use on the maximum number of animals over a period of time.

SUMMARY

Disclosed is an adhesive patch for non-invasively monitoring the health of an animal. The adhesive patch holds a device which can be combined with a system for monitoring the health of an animal or delivering a warning impulse to the animal. The adhesive patch comprises a housing structure containing an opening in that structure or contact with a conductive material for direct electrical contact to the skin of the animal. An adhesive layer is combined to the bottom of the housing structure for adhering the housing structure to the skin of an animal. As part of that housing structure is a pocket accessible through the opening in the housing structure for inserting and holding a warning device in direct contact with the skin of the animal through the opening. The housing structure of the adhesive patch can comprise a base layer comprising a bottom side on which the adhesive layer is attached.

The pocket of the housing structure can further comprise a first material combined to the base layer and a second material combined to the base layer and partially overlapping the first material. The first material can be fixed along three sides to the base layer and the second material can be fixed along three sides to the base layer to combine together to form the pocket above the base layer. A fastener can be provided to selectively close the pocket by combining a fourth side of the first layer with a fourth side of the second layer. Alternatively, the base layer can comprise a top side and a cutout and the pocket can be formed by a first material attached to the top side and surrounding a perimeter of the cutout such that the pocket is accessible from the bottom side of the base layer. In this implementation, the first material has dimensions that correspond to the dimensions of the device, and wherein the first material is attached to the top side of the base layer and inset from the opening so that the device is held in place between the top side of the base layer and the first material.

The housing structure is designed to receive a device with probes that are adapted to be placed in direct contact with the skin of the animal through the opening. The device can have a housing for housing electronics for receiving a signal from a detector for detecting a signal from one or more feeders; a processor in communication with the detector for determining a likely action event from the signal from one or more feeders; and a device in communication with the processor for providing an output through the probes in response to the likely action event.

DETAILED DESCRIPTION

Figure 1:
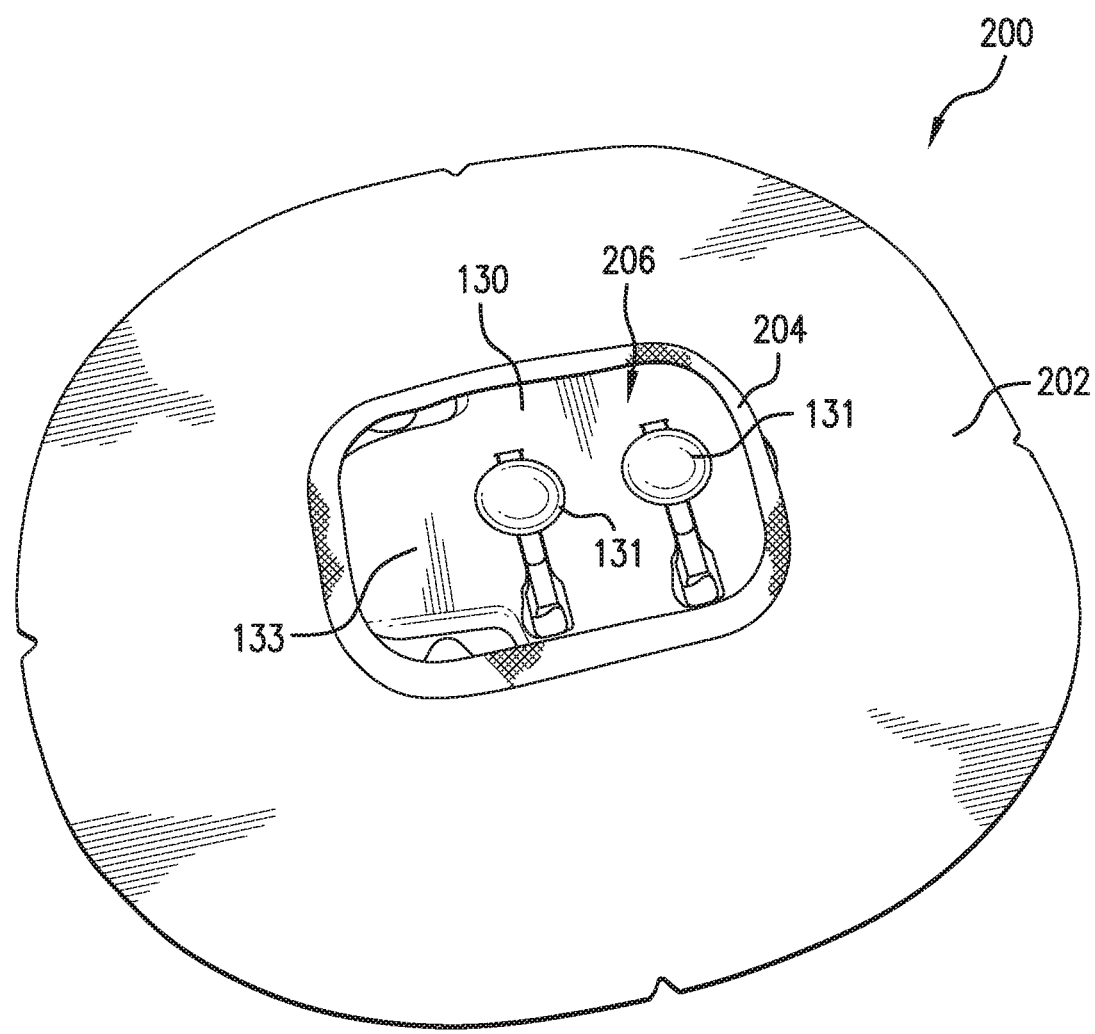
FIG. 1 is a bottom-side perspective view of a disposable housing structure according to this disclosure.
Figure 4:
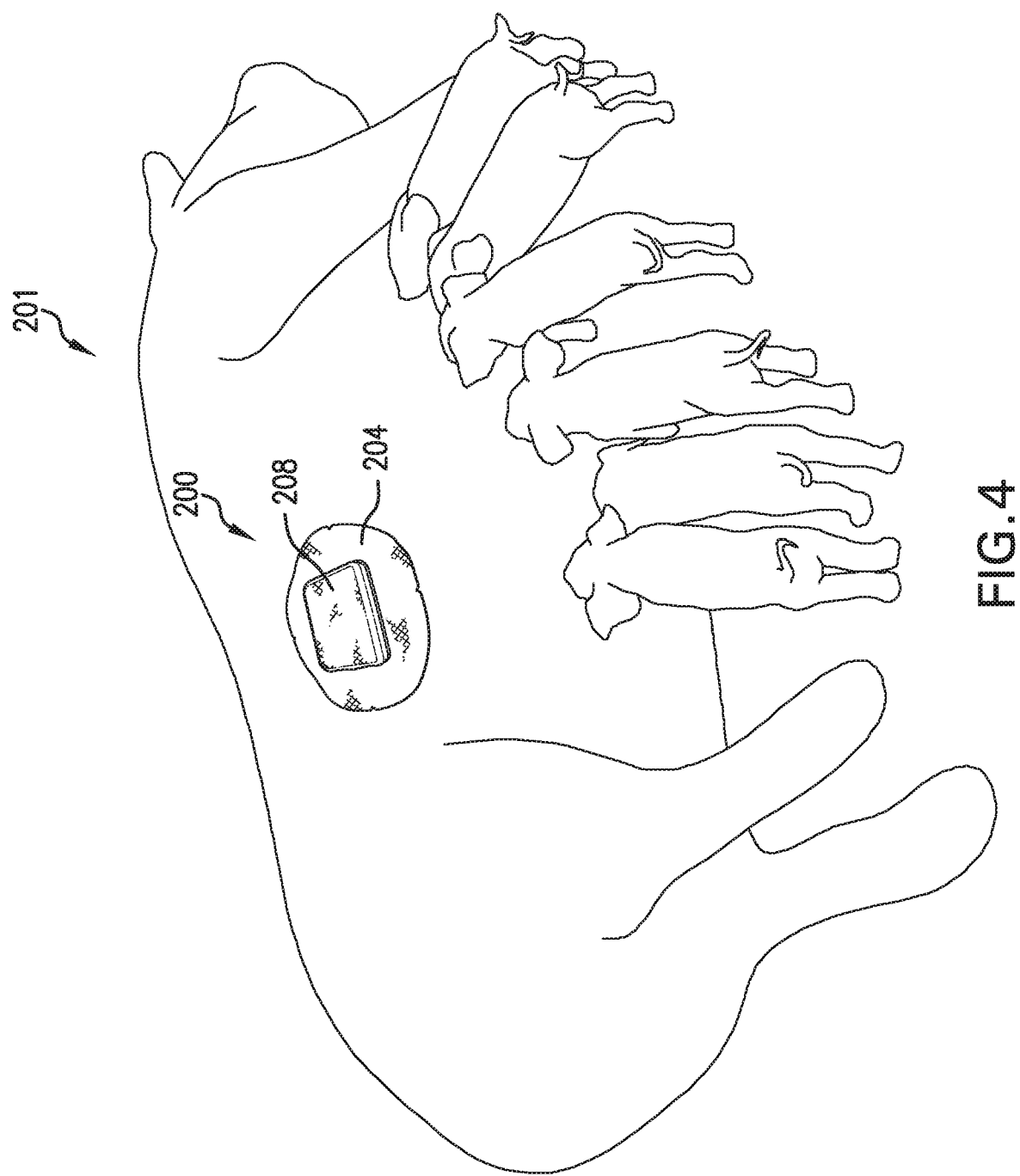
FIG. 4 is a perspective view of the disposable housing structure of FIG. 2 attached to an animal in accordance with this disclosure.

With reference to FIG. 4, disclosed is a disposable housing structure 200 in the form of an adhesive patch that can be attached to the skin of an animal 201 for supporting a removable device 130. Housing structure 200 comprises of an adhesive layer 202 in the form of a medical grade adhesive for adhering to the skin of animal 201. A base layer 204 is combined to adhesive layer 202 with an opening 206 to the skin of animal 201 through which probes 131 (shown in FIG. 1) can extend for contact to the skin of animal 201. A pocket 208 is combined to base layer 204, which is selectively closable for inserting and removing a device 130 that can be placed in direct contact with the skin of animal 201 through opening 206 in base layer 204.

Figure 2:
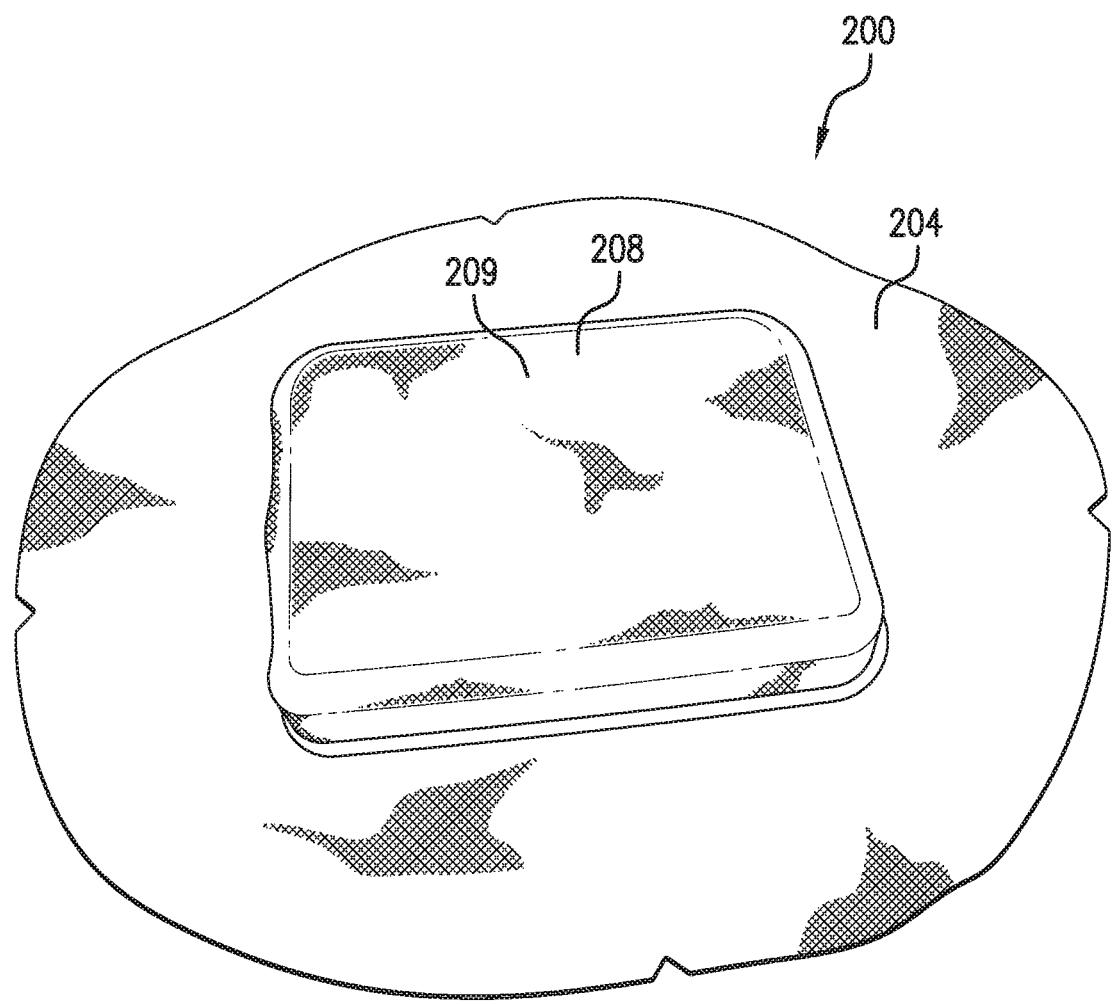
FIG. 2 is a top view of the disposable housing structure of FIG. 1.
Figure 3:
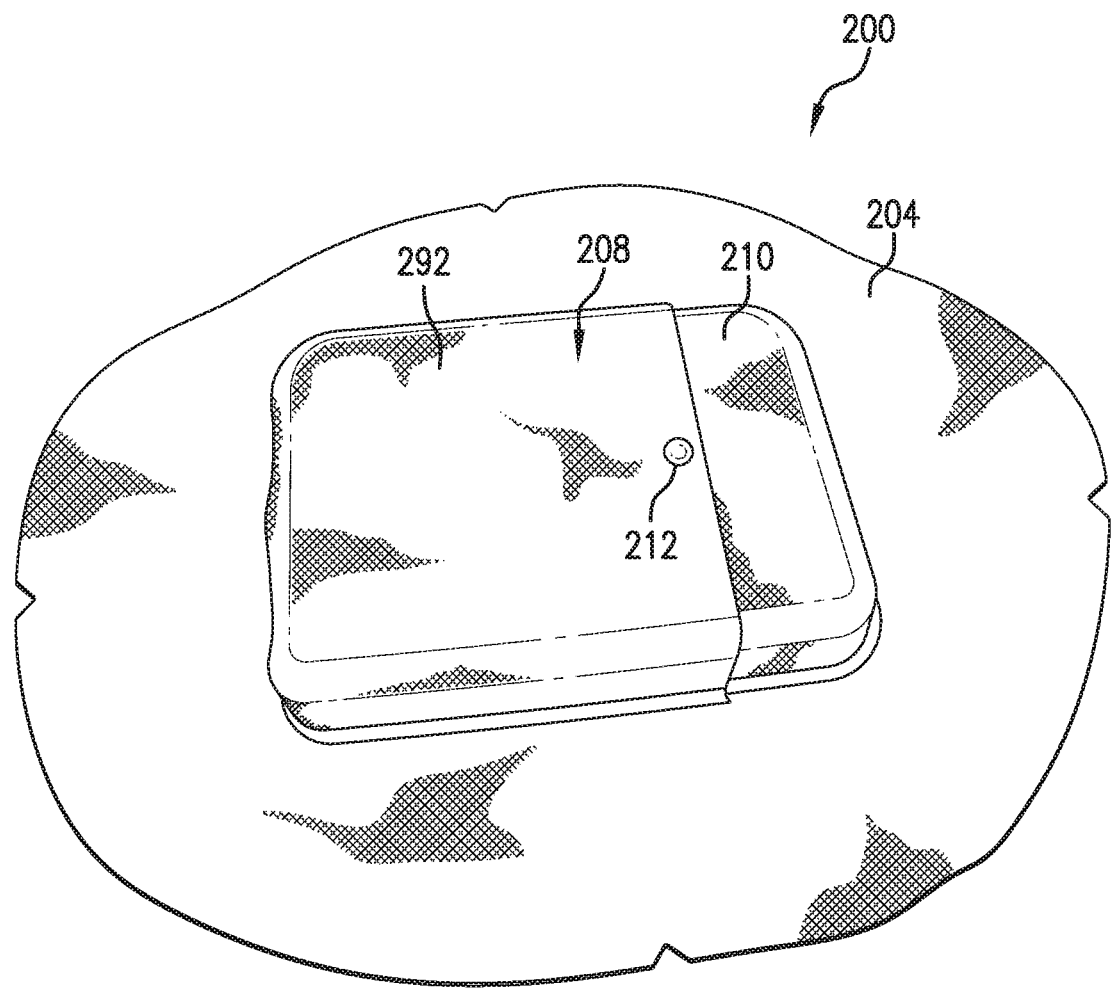
FIG. 3 is a top view of a second embodiment of a disposable housing structure.

More specifically, referring to FIG. 3, pocket 208 can further comprise a first material 210 and a second material 292 partially overlapping first material 210. First material 210 can be fixed along three sides to base layer 204 and second material 292 can be fixed along three sides to base layer 204 to combine pocket 208 to base layer 204. A fastener 212 can be provided to selectively close pocket 208 by combining a fourth side of first material 210 with a fourth side of second material 292. Fastener 212 can be Velcro, a button, a clip, a zipper, etc. First material 210 and second material 292 can be made from any type of material, including cloth or plastic. In an alternative implementation, referring to FIG. 2, pocket 208 can comprise a first material 210 fixed around all its sides to base layer 204.

Underneath base layer 204, with reference back to FIG. 1, is opening 206 to the skin of animal 201 through which probes 131 can extend for contact to the skin of animal 201. Opening 206 can have a diameter or circumference that is smaller than the area of device 130 to receive and hold device 130 in place. Base layer 204 can be made of a stretchable material so that opening 206 can be stretched open to receive device 130. Opening 206 can have a length that is the proximate length of device 130 and a width that is smaller than the width of device 130 so that device 130 can be inserted into opening 206 and turned inside pocket 208 so that it's contained therein. This implementation has the advantage of being made from less material with the disadvantage of prohibiting access to device 130 without removing housing structure 200.

The underside of base layer 204 includes adhesive layer 202. Adhesive layer 202 is a medical-grade adhesive that can be placed on the skin of an animal without irritation or adverse reactions. The adhesive for adhesive layer 202 can be in the form of a tape, foam, liquid, glue, or the like. Examples include solvent-based hot-melt pressure-sensitive type adhesive such as Bostik H/M 9068 (Bostik Inc., Middleton, Mass.) or 3M™ medical tape or adhesive. Prior to use, adhesive on adhesive layer 202 may be protected with a removable release paper facilitating storage and/or transport. Any appropriate or suitable type of release paper can be used. Examples of release papers include papers coated with polyethylene silicone, paraffin wax or aluminum foil.

Figure 5:
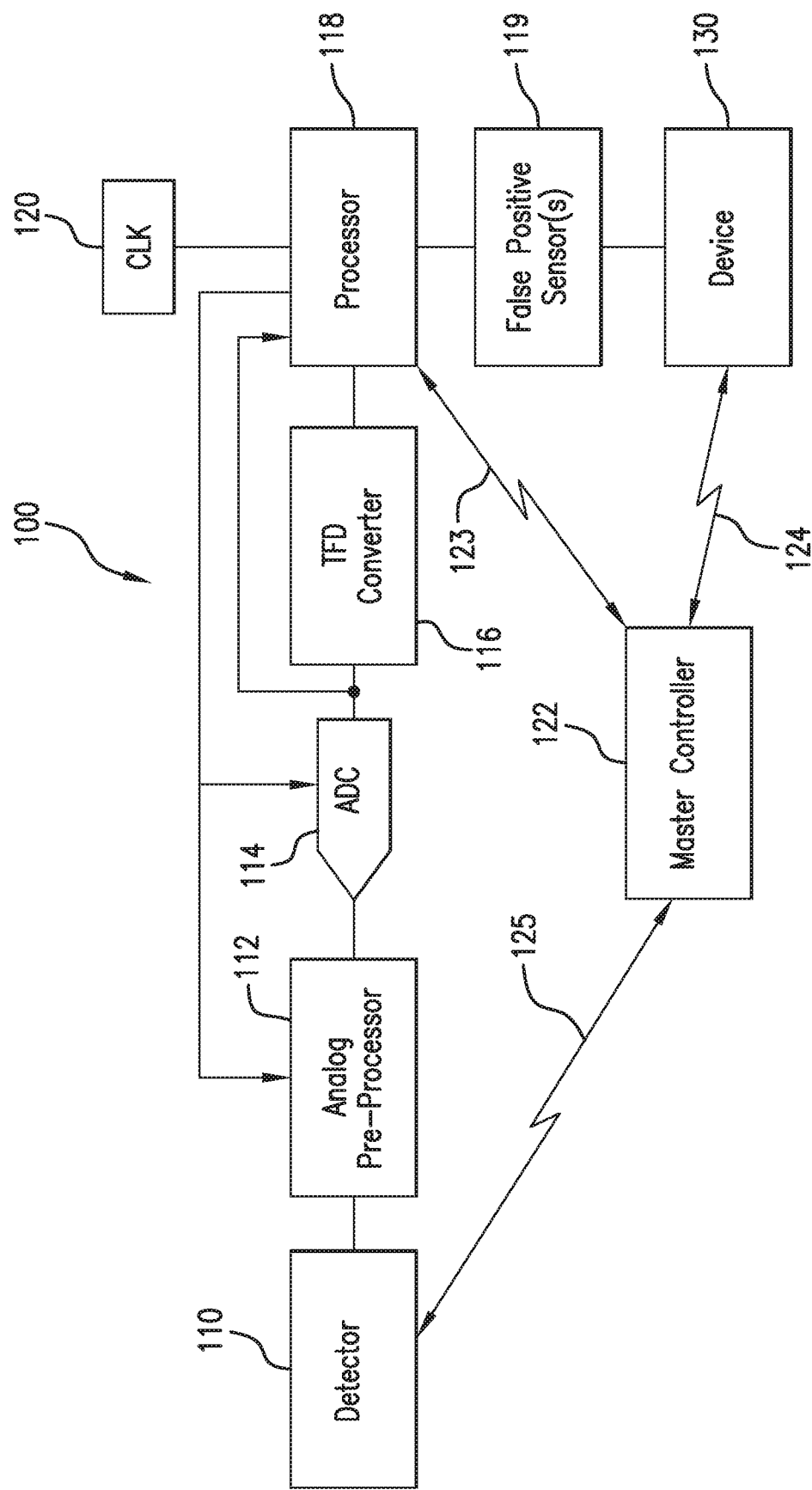
FIG. 5 is a block diagram of the system for preventing injury to feeders by a mother in an animal farrowing location shown generally in FIG. 1.

Disposable housing structure 200 is used in connection with a warning system 100. Warning system 100 includes device 130 that can be selectively inserted and removed from pocket 208 of disposable housing structure 200. Referring to FIG. 5, warning system 100 can include a variety of electronic circuitry, including an analog preprocessor 112 that preprocesses the vibratory signal detected by detector 110 before it is converted into a digital signal by an analog-to-digital convertor ("ADC") 114. The digital representation of the vibratory signal can be processed by a time-to-frequency domain (TFD) converter 116 to derive the frequency contents of the vibratory signal. A processor 118 can be provided for processing the spectral representation of the vibratory signal in the form of a frequency-domain representation of a digitized vibratory signal from ADC 114. A clock 120 can provide the processor 118 timing information for the frequency-domain representation of the digitized vibratory signal. The processor 118 can contain the instruction set necessary to determine when an action event has occurred that requires activation of device 130. Processor 118 can also perform error checking on the action event so that the probability of an accurate action event is more certain. Other electronic devices or programming instructions are also contemplated herein.

Device 130 is shown in communication with processor 118 for providing an output in response to the likely action event. Device 130 stimulates the mother to stand up with an irritation such as an electrical impulse or vibration, or an auditory or visual irritation. In one implementation, device 130 comprises of a "prod" with at least one electrode 131 in contact with the skin of the mother to deliver an electrical impulse. Device 130 can be configured to deliver a multi-stage output wherein a first stage output is an initial irritation to the mother, wherein a second stage output is a stronger irritation. The initial and stronger irritations can be any combination of a vibration or an electrical impulse. Device 130 can also be configured to deliver a positive reinforcement to the mother. Such a positive reinforcement may include sending a signal to a remote feed dispenser to open a feed chute to deliver feed. Finally, device 130 can also be configured to deliver an alert to the producer that there is an issue in farrowing pen 102. Such an alert may include an RF signal to a transceiver 127 (discussed further below) that relays another RF signal directly or indirectly to a phone call with an automated message or text to the producer through landline or to the producer's mobile device. In this instance, the producer would know that a warning has been triggered in a farrowing pen that needs to be checked out.

Device 130 can comprise a bi-directional transceiver for communication with processor 118 over a connection 123 for communicating to processor 118 an "I'm Okay" signal indicative of device functioning properly. The "I'm Okay" signal can also provide a confirmation to processor 118 that the action event was received and the output in response to the action event was provided to the mother. The "I'm Okay" signal can also include a low battery status alert.

Device 130 can be recharged wirelessly in eight hours or less while placed on a recharging platform. Furthermore, device 130 can be paired with processor 118 by sending a special pairing identification command while placed upon a charging platform, after which device 130 confirms with both a wireless response to processor 118 and a visual confirmation to the operator by blinking the status LED indicator rapidly.

Housing 133 for device 130 can also include detectors such as biometric sensors; for example, housing 133 can contain a heartbeat signal to provide visual indication that the housing with device 130 is ready to receive a signal and conserving power with the indicator light flashing once for every one to five seconds in 50 ms bursts. Housing 133 can also contain a temperature sensor (as discussed above) to monitor the skin temperature of the mother, a multi-axis gyroscope to monitor relative attitude of the mother, which can be used to determine whether the mother is standing up or lying down, an accelerometer (as discussed above) to monitor motion and any changes in motion, which can be used to determine how active the mother is and to approximate the position and directional attitude of the mother, and an RFID for identification. This biometric sensor data can be sent to processor 118 for later analysis or for downloading by the operator.

In use, the housing structure 200 is attached to the animal, by first cleaning the hide of loose hair, dander, dirt and other particles from the animal. If not already installed, device 130 placed inside pocket 208, and, if not already removed, remove the release paper from housing structure 200 and position and apply the patch to animal 201, pressing it into place using either finger pressure.

Together warning system 100 and housing structure 200 provides an affordable way for the operator to quickly combine a warning system to the mother in a safe and reliable way that allows the operator to quickly remove the warning system after it is no longer needed for use with another mother. Overtime, adhesive layer 202 on housing structure 200 may degrade and housing structure 200 will fall off of the mother.

Base layer 204 and/or pocket 208 of housing structure 200 can be made of any material, including, but not limited to, fabric, cloth, plastic, metal, or any combination thereof. The illustrated embodiment shows animal 201 in the form of a sow with nursing piglets. It should be understood that animal 201 can be any animal, including a human. The instant disclosure is applicable whenever there is a need to attach a removable or reusable device 130 to such animal 201.

Reference may also have been made throughout this disclosure to "one embodiment," "an embodiment," or "embodiments" meaning that a particular described feature, structure, or characteristic is included in at least one embodiment of the present invention. Thus, usage of such phrases may refer to more than just one embodiment. Furthermore, the described features, structures, or characteristics may be combined in any suitable manner in one or more embodiments.

While the present invention has been particularly shown and described with reference to exemplary embodiments thereof, it should be understood by those of ordinary skill in the art that various changes, substitutions and alterations can be made herein without departing from the spirit and scope of the invention as embodied by the appended claims and their equivalents.

The invention claimed is:

1. An adhesive patch for non-invasively monitoring a health of an animal, the adhesive patch comprising:
   a first state without a warning device and comprising a housing structure comprising a base layer with a first opening, wherein the base layer comprises a stretchable material so that the first opening can be stretched;
   an adhesive layer comprising a second opening combined to a bottom of the housing structure on the base layer with the second opening aligned with the first opening and comprising a stretchable material so that the second opening can be stretched and for adhering the housing structure to a skin of the animal;
   a removable release paper combined to the adhesive layer to protect the adhesive layer when the adhesive patch is in the first state; and
   a pocket accessible through the first opening in the housing structure and through the second opening in the adhesive layer for inserting and holding the warning device in direct contact with the skin of the animal through the first opening and the second opening; and
   a second state comprising the housing structure with the adhesive layer and the removable release paper removed from the adhesive layer and the pocket with the warning device where the adhesive patch is configured for placement in direct contact with the skin of the animal.

2. The adhesive patch of claim 1, wherein the housing structure further comprises of the base layer comprising a bottom side on which the adhesive layer is attached.

3. The adhesive patch of claim 1, wherein the device further comprises probes that are adapted to be placed in direct contact with the skin of the animal through the first opening.

4. The adhesive patch of claim 3, wherein the device comprises of a housing for housing electronics for receiving a signal from a detector for detecting a signal from one or more feeders; a processor in communication with the detector for determining a likely action event from the signal from one or more feeders; and a device in communication with the processor for providing an output through the probes in response to the likely action event.

5. A system for monitoring a health of an animal, the system comprising:
   an adhesive patch comprising a first state and a second state, the first state without a warning device and comprising:
   a housing structure comprising a base layer with a first opening, wherein the base layer comprises a stretchable material so that the first opening can be stretched;
   an adhesive layer comprising a second opening combined to a bottom of the housing structure with the second opening aligned with the first opening and comprising a stretchable material so that the second opening can be stretched and for adhering the housing structure to a skin of the animal;
   a removable release paper combined to the adhesive layer to protect the adhesive layer when the adhesive patch is in the first state; and
   a pocket accessible through the first opening in the housing structure and through the second opening in the adhesive layer; and
   the second state of the adhesive patch comprising the housing structure with the adhesive layer and the removable release paper removed from the adhesive layer and the pocket with the warning device in the pocket of the adhesive patch in direct contact with the animal through the first opening in the housing structure and the second opening in the adhesive layer.

6. The system of claim 5, wherein the base layer of the adhesive patch further comprises of a top side and a cutout and the pocket is formed by a first material attached to the top side and surrounding a perimeter of the cutout such that the pocket is accessible from a bottom side of the base layer, wherein the first material has dimensions that correspond to dimensions of the device, and wherein the first material is attached to the top side of the base layer and inset from the opening so that the device is held in place between the top side of the base layer and the first material.

7. The system of claim 6, wherein the device further comprises probes that are adapted to be placed in direct contact with the skin of the animal through the opening of the housing structure of the adhesive patch and wherein the device comprises of a housing for housing electronics for receiving a signal from a detector for detecting a signal from one or more feeders; a processor in communication with the detector for determining a likely action event from the signal from one or more feeders;
   and a device in communication with the processor for providing an output through the probes in response to the likely action event.

8. An adhesive patch for non-invasively monitoring a health of an animal, the adhesive patch comprising a first state and a second state, the first state of the adhesive patch without a warning device and comprising:
   a housing structure comprising a base layer with a top side and a bottom side with a first opening in the bottom side of the base layer, wherein the base layer comprises a stretchable material so that the first opening can be stretched;
   an adhesive layer comprising a second opening combined to the bottom side of the base layer with the second opening aligned with the first opening and comprising a stretchable material so that the second opening can be stretched and for adhering the housing structure to a skin of the animal;

a removable release paper combined to the adhesive layer to protect the adhesive layer when the adhesive patch is in the first state; and a pocket accessible through the first opening in the base layer and through the second opening in the adhesive layer for inserting and holding a device in direct contact with the skin of the animal through the first opening on the bottom side of the housing structure; and a second state comprising the housing structure with the adhesive layer and the removable release paper removed from the adhesive layer and the pocket with the warning device where the adhesive patch is configured for placement in direct contact with the skin of the animal.

9. The adhesive patch of claim 8, wherein the pocket is formed by a first material attached to the top side of the base layer around the opening such that the pocket is accessible from the bottom side of the base layer through the opening, and wherein the first material has dimensions that correspond to dimensions of the device, and wherein the first material is attached to the top side of the base layer and inset from the opening so that the device is held in place between the top side of the base layer and the first material.

10. The adhesive patch of claim 8, wherein the device further comprises probes that are adapted to be placed in direct contact with the skin of the animal through the opening of the base layer, and wherein the device comprises of a housing for housing electronics for receiving a signal from a detector for detecting a signal from one or more feeders; a processor in communication with the detector for determining a likely action event from the signal from one or more feeders; and a device in communication with the processor for providing an output through the probes in response to the likely action event.

* * * * *